Sept. 5, 1967 M. L. MEILLAND Plant Pat. 2,764
ROSE PLANT
Filed June 2, 1966
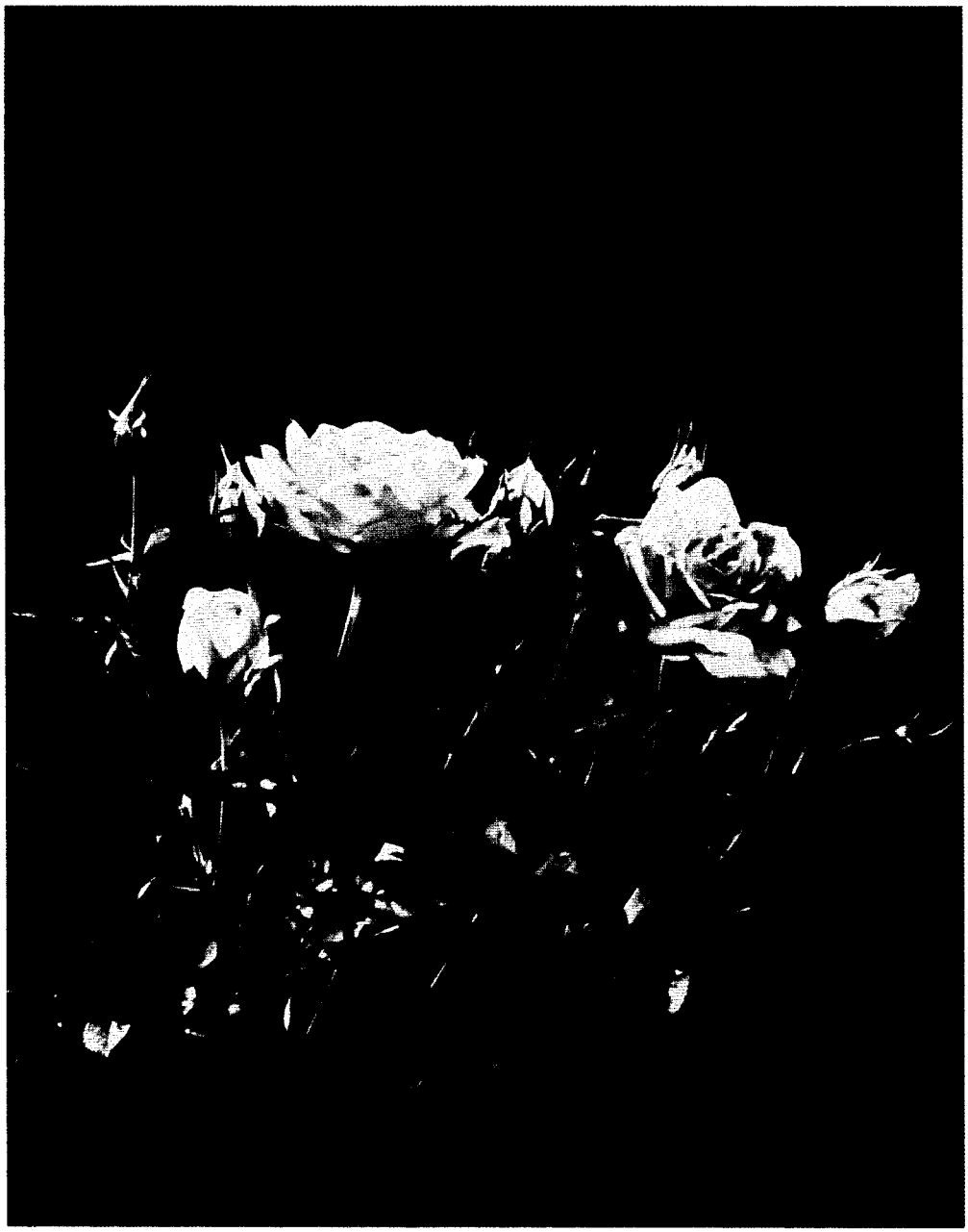
Inventor.
Marie Louise Meilland
By: Robb & Robb
Attorneys.

United States Patent Office

Plant Pat. 2,764
Patented Sept. 5, 1967

2,764
ROSE PLANT

Marie Louise Meilland, Cap d'Antibes, Alpes-Maritimes, France, assignor to The Conard-Pyle Company, West Grove, Pa., a corporation of Pennsylvania Filed June 2, 1966, Ser. No. 554,914
1 Claim. (Cl. Plt.—9)

The present invention relates to a new and distinct variety of rose plant of the miniature class, which was originated by me by crossing an unnamed and unpatented seedling of "Dany Robin" (unpatented) × "Fire King" (U.S. Plant Patent No. 1,758) with the variety known as "Perle de Montserrat" (unpatented).

As the result of this breeding, I have produced a new and improved rose variety which is distinguished from its parents, as well as from all other varieties of which I am aware, as evidenced by the following unique combination of characteristics which are outstanding therein:

(1) A vigorous habit of growth for a rose of this type;
(2) Production of relatively large flowers of high-centered form at the beginning, but becoming flat, with the petals loosely rolled outward from the beginning to maturity;
(3) A relatively high flower petal count usually ranging between 65 and 75 petals; and
(4) A distinctive and attractive Salmon Pink general color tonality of the flowers.

In comparison with its unnamed seedling parent, the new variety is classified as a miniature instead of a floribunda rose like the parent, and its general color tonality is Salmon Pink as distinguished from the bicolored flowers of the parent which are Rose Red on the inside and Amber White on the reverse.

As compared with its pollen parent "Perle de Montserrat," the new variety is more vigorous and taller growing in its habit, and the flowers are Salmon Pink in color instead of Deep Red like those of this parent.

Asexual reproduction of the new variety by both cuttings and budding, as performed in France and at West Grove, Pa., U.S.A., shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of the new variety, with color terminology in accordance with the Horticultural Colour Chart of the Royal Horticultural Society, except where general color terms of ordinary dictionary significance are obvious:

Type: Hardy, dwarf; outdoor; seedling; for garden decoration.
Class: Miniature.
Breeding: Seedling.
*Seed parent.*—An unnamed seedling of "Dany Robin" × "Fire King."
*Pollen parent.*—"Perle de Montserrat."
Propagation: Holds its distinguishing characteristics through succeeding propagations by both cuttings and budding.

*Flower*

Locality where grown and observed: West Grove, Pa., U.S.A.
Flowers borne: Both singly and several to stem; in irregular clusters; on short stems of normal strength.
Quantity of bloom: Free, both outdoors and in greenhouse.

Continuity: Continuous.
Fragrance: Very slight.
Bud:
*Peduncle.*—Short; slender; erect; almost smooth; with medium number of glandular tipped hairs. Color—green, overlying red-green.
*Before calyx breaks.*—Size—small. Form—short; ovoid; with conspicuous neck; with foliaceous appendages on the surface of the bud; with slender bristle-like foliaceous parts extending beyond the tip of the bud equal to ¼ or more of its length.
*As calyx breaks.*—Color—Chrysanthemum Crimson, Plate 824/1.
*As first petal opens.*—Size—small. Form—medium length; ovoid. Color—outside: Claret Rose, Plate 021/1 over outer ¾ of petal, blending to Claret Rose, Plate 021/2 and then to Sap Green, Plate 62/3; inside: Delft Rose, Plate 020/1, abruptly changing to Sap Green, Plate 62/3 over the basal ⅕ of the petal.
*Opening.*—Opens up well.
Bloom:
*Size (when fully open).*—Large for miniature class; from 1¾ inches to 2 inches.
*Petalage.*—Very double; from 65 to 75 petals; arranged regularly.
*Form.*—High-centered at first, but becoming flat; petals being at first loosely rolled outward and remaining loosely rolled outward at maturity.
Petals:
*Texture.*—Medium thickness.
*Appearance.*—Inside—satiny. Outside—satiny.
*Shape.*—Outer—roundly obovate and generally with one notch. Intermediate—roundly obovate and generally with one notch. Inner—obovate and generally no notches.

This description of a newly opened flower was made from a rose grown in a greenhouse during the month of April at West Grove, Pa., U.S.A.:

*Color.*—Outer petal—outside surface: Crimson, Plate 22/1, veined with near white over upper ⅔ of petal and changing abruptly to Sap Green, Plate 62/3 over basal ⅓ of petal; inside surface: Carmine Rose, Plate 621, blending to Carmine Rose, Plate 621/1, with base Sap Green, Plate 62/3. Intermediate petal—outside surface: Crimson, Plate 22/1, lightly veined with off-white over the upper ⅔, changing abruptly to Sap Green, Plate 62/3; inside surface: Claret Rose, Plate 021 over upper half of petal, becoming tinted with Claret Rose, Plate 021/2 and changing abruptly to Sap Green, Plate 62/3 over basal ¼ of petal. Inner petal—outside surface: Claret Rose, Plate 021 at apical margin blending to Carmine, Plate 21/1 and to Carmine, Plate 21/2, changing abruptly to Sap Green, Plate 62/3 over basal ⅕; inside surface: Claret Rose, Plate 021 at apical margin, blending to Empire Rose, Plate 621, and changing abruptly to Sap Green, Plate 62/3 over basal ¼ of petal.

This description was made from a rose that was open for three days in a greenhouse during the month of April at West Grove, Pa., U.S.A.:

*Color.*—Outer petal—outside surface: Crimson, Plate 22/3, changing abruptly to Sap Green, Plate 62/3; inside surface: Carmine Rose, Plate 621, blending to Carmine Rose, Plates 621/1 and 621/2, and then changing abruptly to Sap Green, Plate 62/3. Inner petal—outside surface: Crimson, Plate 22/2, changing abruptly to Sulphur Yellow, Plate 1/1 over basal ⅛ of petal; inside surface: Rose Opal, Plate 022/1, changing abruptly to Sulphur Yellow, Plate 1/1 over basal ⅛ of petal.

*General color effect.*—Newly opened flower—Carmine, Plate 21/1. Three days open—near Neyron Rose, Plate 623.

*Behavior.*—Persist.

*Flower longevity.*—Cut roses grown in greenhouse and kept at living room temperatures—5 days in April.

*Reproductive organs*

Stamens: Medium number; arranged irregularly about pistils; mixed with petaloids.

Filaments: Short; most with anthers.

*Color.*—Greenish yellow.

Anthers: Very small; all open at once; occasionally an anther fused with a petaloid.

*Color.*—Yellow.

Pollen: Sparse.

*Color.*—Yellow.

Pistils: Medium number.

Styles: Uneven; very short; thin; loosely bunched.

Stigma:

*Color.*—Reddish-brown.

Ovaries: Some protruding from receptacle.

Hips: None observed.

Sepals: Permanent; from short to medium length; spear-shaped.

Seeds: None observed.

*Plant*

Foliage:

*Leaves.*—Compound of 5–7 leaflets; normal abundance; moderately large for class; thin; leathery.

*Leaflets.*—Shape—oval. Apex—acute. Base—obtuse. Margin—simply serrate.

*Color.*—Mature—upper surface: Spinach Green, Plate 0960, with narrow maroon border; under surface: Lavender Green, Plate 000761. Young.—upper surface: Spinach Green, Plate 0960/1, with sharply defined red margin; under surface: Scheele's Green, Plate 860, varyingly overlaid with red.

*Rachis (the supporting stem of the compound leaf).*—Light. Upper side—grooved; hairy. Under side—sparsely thorny.

*Stipules.*—Moderately long; narrow; with moderately long points turning out at an angle of more than 45°.

*Disease resistance.*—Comparable to that of the average variety grown under the same cultural conditions at West Grove, Pa., U.S.A.

Growth:

*Habit.*—Dwarf; upright; much-branched.

*Growth.*—Free.

*Canes.*—Light.

*Main stems.*—Bright. Color—Spinach Green, Plate 0960/1. Prickles—few; color: reddish. Hairs—none.

*Branches.*—Bright. Color—Spinach Green, Plate 0960/1. Prickles—Few; color: reddish. Hairs—none.

*New shoots.*—Dull. Color—Spinach Green, Plate 0960, with reddish overcast. Prickles—few; color: reddish. Hairs—none.

I claim:

A new and distinct variety of rose plant of the miniature class, substantially as herein shown and described, characterized particularly as to novelty by the unique combination of a vigorous habit of growth for a rose of this type, production of relatively large flowers of high-centered form at the beginning, but becoming flat, with the petals loosely rolled outward from the beginning to maturity, a relatively high flower petal count usually ranging between 65 and 75 petals and a distinctive and attractive Salmon Pink general color tonality of the flowers.

No references cited.

ABRAHAM G. STONE, *Primary Examiner.*

ROBERT E. BAGWILL, *Examiner.*